(12) United States Patent
Andrews et al.

(10) Patent No.: US 6,943,358 B1
(45) Date of Patent: Sep. 13, 2005

(54) METHOD FOR DEVELOPING A CALIBRATION ALGORITHM FOR QUANTIFYING THE HYDROCARBON CONTENT OF AQUEOUS MEDIA

(75) Inventors: John M. Andrews, San Diego, CA (US); Stephen H. Lieberman, La Mesa, CA (US); Li-Ming He, San Diego, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 129 days.

(21) Appl. No.: 10/318,669

(22) Filed: Dec. 5, 2002

Related U.S. Application Data

(63) Continuation-in-part of application No. 09/814,089, filed on Mar. 21, 2001, now Pat. No. 6,525,325.

(51) Int. Cl.$^7$ .................................................. G01T 1/10
(52) U.S. Cl. ................................................. 250/459.1
(58) Field of Search .......................... 250/461.1, 372, 250/573, 574, 301

(56) References Cited

U.S. PATENT DOCUMENTS

| | | | | |
|---|---|---|---|---|
| 5,420,432 A | * | 5/1995 | Manook et al. | 250/373 |
| 5,703,959 A | * | 12/1997 | Asano et al. | 382/133 |
| 5,717,209 A | * | 2/1998 | Bigman et al. | 250/339.12 |

* cited by examiner

*Primary Examiner*—David Porta
*Assistant Examiner*—Marcus Taningco
(74) *Attorney, Agent, or Firm*—Peter A. Lipovsky; Michael A. Kagan; Allan Y. Yee

(57) ABSTRACT

A method for developing an algorithm for quantifying the hydrocarbon content of aqueous media includes: a) irradiating aqueous test samples containing hydrocarbons and particulates with light so that fluorescent emissions and scattered light signals are emitted from the test samples; b) detecting fluorescent emissions and the scattered light signals emitted from the test samples; c) generating first data signals representing the intensities of the fluorescent emissions, and second data signals representing the intensities and scatter angles of the second data signals; d) storing representations of the first and second data signals to create a data set; e) dividing the data set into training, test, and validation data sets; f) selecting input parameters from the data set; g) defining and training a neural network having hidden node using the training and the test data sets; and h) validating the neural network using the validation data set.

4 Claims, 7 Drawing Sheets

| DATA RECORD | SAMPLE | PPM | VECTORIZED DATA SET | | |
|---|---|---|---|---|---|
| | | OIL CONTENT (ppm) | FLUORESCENCE | | |
| | | | FLUORESCENCE INTENSITY AT 280nm | FLUORESCENCE INTENSITY AT 300nm | FLUORESCENCE INTENSITY AT 320nm |
| 1 | DFM | 5 | 35 | 56 | 17 |
| 2 | DFM | 25 | 200 | 312 | 92 |
| 3 | JP5 | 5 | 100 | 20 | 32 |
| 4 | JP5 | 25 | 516 | 101 | 158 |
| 5 | WATER | 0 | 4 | 6 | -2 |

FIG. 3A

| FIG 3 | FIG. 3A | FIG. 3B |
|---|---|---|

| PARTICLE SIZE (FROM SCATTERING DATA) | | |
|---|---|---|
| VOLUME CONCENTRATION 2-5 micron | VOLUME CONCENTRATION 5-10 micron | VOLUME CONCENTRATION 10-20 micron |
| 2 | 2 | 1 |
| 11 | 9 | 2 |
| 1 | 2 | 0 |
| 4 | 10 | 1 |
| 1 | 0 | 0 |

FIG. 3B

METHOD FOR DEVELOPING A CALIBRATION ALGORITHM FOR QUANTIFYING THE HYDROCARBON CONTENT OF AQUEOUS MEDIA

This is a continuation-in-part of application Ser. No. 09/814,089, entitled A System For Quantifying the Hydrocarbon Content of Aqueous Media, filed 21 Mar. 2001.

BACKGROUND OF THE INVENTION

Many industrial processes utilize an oil-content-monitor (OCM) to provide a real-time on-line measure of the amount of petroleum hydrocarbons present in process water or wastewater streams. Bilge discharge monitoring is a common example of OCM usage. Ships at sea treat bilge water to remove oily contaminants prior to discharging the bilge into the surrounding environment. Environmental regulations specify that bilge water may not be pumped overboard if the oil content exceeds 15 part-per-million (ppm) within the coastal zone, or 100 ppm at sea. Shipboard OCMs provide on-line measurements of the amount of fuel or oil present in the treated bilge water. The ship's crew utilizes this information to make ongoing decisions as to whether the processed bilge may be lawfully discharged or requires further treatment. Examples of other OCM applications include on-line monitoring of: oil well process water discharge, car/aircraft wash facilities, power plant effluent, engine cooling water, desalination plant intake, boiler condensate, storm water runoff, and reclaimed groundwater.

Many existing OCM systems use optical methods to measure oil content. OCM sensors based on ultraviolet (UV) fluorescence, optical scattering, or optical transmission/absorption methods are common. Optical techniques have a "stand-off" advantage over other methods in that direct physical contact with the sample is unnecessary.

Most optically based OCMs are single-channel (zero order) instruments, i.e. they utilize one measured parameter to determine hydrocarbon content. The single parameter these instruments measure may include fluorescence emission at a single wavelength band, or suspended-particle scattering at a single angle, or optical absorption at a single wavelength band, or the ratio of single-angle scattering to single wavelength-band transmission, etc. Instrument calibration is performed by applying a mathematical transformation of the single measured datum in order to relate the raw signal to actual oil content. Single channel instruments offer the benefit of a simple univariate calibration model, e.g. the calibration is typically implemented as a linear function of system response.

Accurate quantification when the hydrocarbon species and matrix are not known a priori is simply not possible with single-channel (univariate calibration) methods. Single-channel (univariate calibration) instruments are adequate for applications where the hydrocarbon analyte, aqueous matrix, and mixing conditions are all well characterized and do not vary over time. However, as single-channel instruments they cannot provide accurate oil content measurements when any of the following conditions exist: a) when the type of hydrocarbon analyte is unknown or changing, b) when the background signal is varying, c) when matrix effects are present (i.e. when the sensitivity of the analyte is dependent upon the presence of other species), or d) when physical factors that effect emulsification, e.g. mechanical stirring, temperature, etc. vary. The inaccuracies are due to the fact that a single data point provides insufficient information to resolve multiple unknown parameters. If the instrumental sensitivity is significantly different for two or more types of petroleum products, for example diesel fuel and lube oil, and both are potentially present in the sample, then a given instrumental response cannot be uniquely associated with a single "overall" oil content. Single-channel instruments are also incapable of distinguishing between a signal arising from target analytes and background interference. Signal changes brought about by spectral or physical interferences, common in many applications, cannot be differentiated from signal changes arising from a change in oil content. In a dynamic environment, this leads to erroneous determinations of oil content.

Accurate measurement of small quantities of oil in water (e.g. low mg $L^{-1}$) is extremely difficult when the hydrocarbon type and/or matrix is changing or when physical and chemical interferences are present. Therefore, a need exists for an accurate and reliable method for determining the concentration of oil droplets in aqueous media.

SUMMARY OF THE INVENTION

A method for developing an algorithm for quantifying the hydrocarbon content of aqueous media includes: a) irradiating aqueous test samples containing hydrocarbons and particulates with light so that fluorescent emissions and scattered light signals are emitted from the test samples; b) detecting fluorescent emissions and the scattered light signals emitted from the test samples; c) generating first data signals representing the intensities of the fluorescent emissions, and second data signals representing the intensities and scatter angles of the second data signals; d) storing representations of the first and second data signals to create a data set; e) dividing the data set into training, test, and validation data sets; f) selecting input parameters from the data set; g) defining and training a neural network having hidden nodes using the training and the test data sets; and h) validating the neural network using the validation data set.

Advantages of the invention will become more apparent upon review of the accompanying drawings and specification, including the claims.

BRIEF DESCRIPTION OF THE DRAWINGS

FIG. 3 is an example of a data vector that associates levels of hydrocarbon contamination to actual spectral and particulate size data for several liquid test samples.

Throughout the several views, like elements are referenced using like references.

DESCRIPTION OF THE PREFERRED EMBODIMENT

Figure 1:
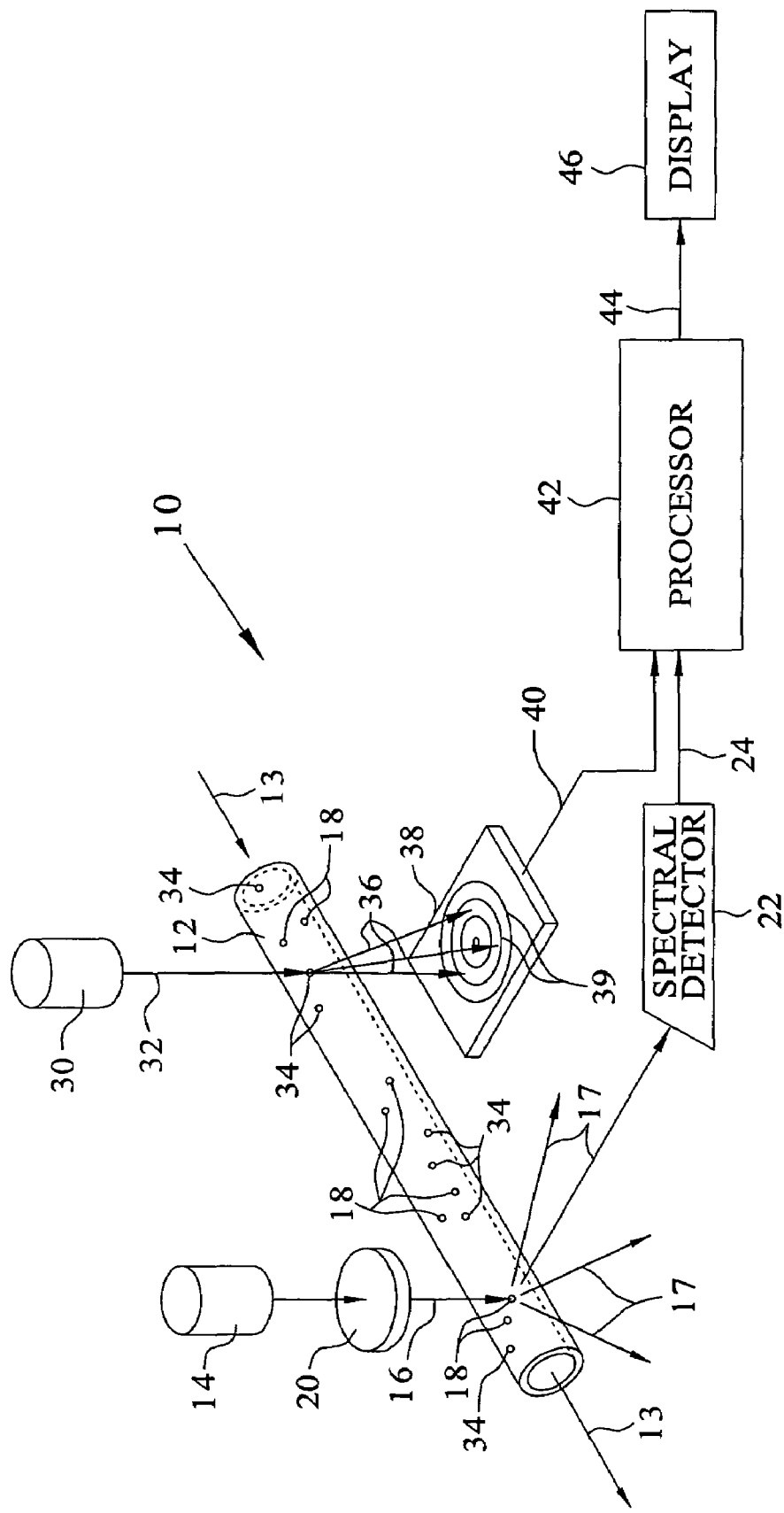
FIG. 1 shows a system for quantifying the petroleum content of aqueous media that embodies features of the present invention.

The present invention is directed to the development of a calibration algorithm that is used in a system 10 for quantifying the hydrocarbon content of aqueous media. Referring to FIG. 1, system 10 includes a sample cell 12, which may be implemented as a transparent tube, in which is present an aqueous sample 13. The sample cell 12 may be made of a transparent material such as quartz or glass that is generally chemically inert to hydrocarbons. The sample cell 12 may also be implemented in aluminum, Teflon®, or stainless steel and have transparent windows, not shown, for allowing the penetration and emission of light between the interior and exterior of the cell. A light source 14 generates a light signal 16 having ultraviolet components. Light signal 16 is directed into sample cell 12 to stimulate fluorescent emissions 17 from any hydrocarbons 18 that may be present in the aqueous sample 13 that are irradiated by light signal 16. Light source 14 may be economically implemented as a broadband light source, such as a xenon flashlamp, in which case light signal 16 is a broadband light beam having multi-spectral, including ultraviolet, components. An optical filter or monochrometer 20 may be used to limit the spectral bandpass of light signal 16. However, light source 16 may also be implemented using any UV source such as a deuterium lamp, light emitting diode, or laser. Multiple light sources as well as multiple excitation energies could be used to enhance selectivity. In response to detecting fluorescent emission signals 17, a spectral detector 22 generates electrical signals 24 that represent one or more spectral components of signal 17 having different wavelengths for characterizing fluorescent emission signals 17. Spectral detector 22 may be implemented as a spectrograph (or monochrometer or optical filter array) coupled photodiode, photodiode array, CCD, photomultiplier tube (PMT), or multianode PMT. In the preferred embodiment, the field of view of the spectral detector 22 is oriented so that the path of light signal 16 does not excite the spectral detector 22. For example, the path of light signal 16 may be orthogonal to a vector that is normal to the light sensing surface of detector 22.

System 10 relies on multi-angle optical scattering techniques for determining the size-distribution of droplets 34 in aqueous test sample 13. Droplets 34 may be emulsified hydrocarbons, generally in the form of oil droplets, in aqueous test sample 13. Hereinafter, the references to hydrocarbons and oil droplets may be used interchangeably. Analysis of the sizes of droplets 34 is achieved by measuring the intensity of scattered light signals 36 at many (32) angles, as for example, between 0.1 and 20 degrees. Coherent light source 30 generates a coherent light signal 32 that is directed into sample cell 12. If light signal 32 irradiates any emulsified oil droplets 34 that may be suspended in aqueous test sample 13, the interaction between the light signal 32 and the droplets or particulates 34 causes the light signal 32 to become divided into scattered light signals 36. Scattering refers to the transformation of coherent light signal 32 into many light signals 36 that propagate at an angle with respect to the direction of coherent light signal 32. Scattered light signals 36 are detected by multi-angle photodetector 38, such as a ring detector, charge couple device (CCD), or photodiode array, from which is determined the intensity and angle of scatter for each detected scattered light signal 36 with respect to the direction of coherent light signal 32. The multi-angle photodetector 38 generates electrical signals, collectively referenced as signal 40 from locations on the photodetector 38 where the scattered light signals 36 irradiate light detecting elements 39. Signal 40 represents the intensities and scatter angles of light signals 36 that are detected by light scattering detector 38. Software executed in processor 42 employs the information encoded in signal 40 to determine the size distribution of oil droplets 34 in aqueous test sample 13 using well known techniques. Software for determining particle size distribution from optical intensities and scatter angles of light passing through a liquid is available from Sequoia Scientific, Inc.

Processor 42 implements a calibration algorithm that uses the particle size distribution of oil droplets 34 previously determined by processor 42 using intensity and scatter angle information encoded in signal 40, and the spectral component information from flourescent emission signals 17 represented in signals 24 to determine a value representing the hydrocarbon concentration content $H_c$ of hydrocarbons 34 present in the aqueous test sample 13. Implementation of the algorithm by processor 42 results in the generation of an output signal 44 representing the hydrocarbon concentration content $H_c$ of oil in test sample 34 that is provided to display 46. Display 46 presents $H_c$ in human readable form, as for example, "Oil content=25 ppm." By way of example, display 46 may be implemented as a video monitor, a printer, a strip chart recorder, and the like.

The development of the calibration algorithm is described with reference to FIGS. 2 and 6. First, the types of fluids, degrees of contamination, and matrix conditions are established for a particular monitoring application at step 50. FIG. 3 illustrates a table of example data for various mixtures and types of fluids that have predetermined levels of hydrocarbon contamination and particle size contamination that encompass the scope of the levels of contamination of test samples 13 likely to be examined by sensor 10. For example, the range of hydrocarbon contamination, typically measured in parts per million (ppm), in test sample 13 may range from 0 parts per million (ppm) to 25 ppm, and the size-distribution particulates 34 may range from 0 to 20 microns.

Figure 2:
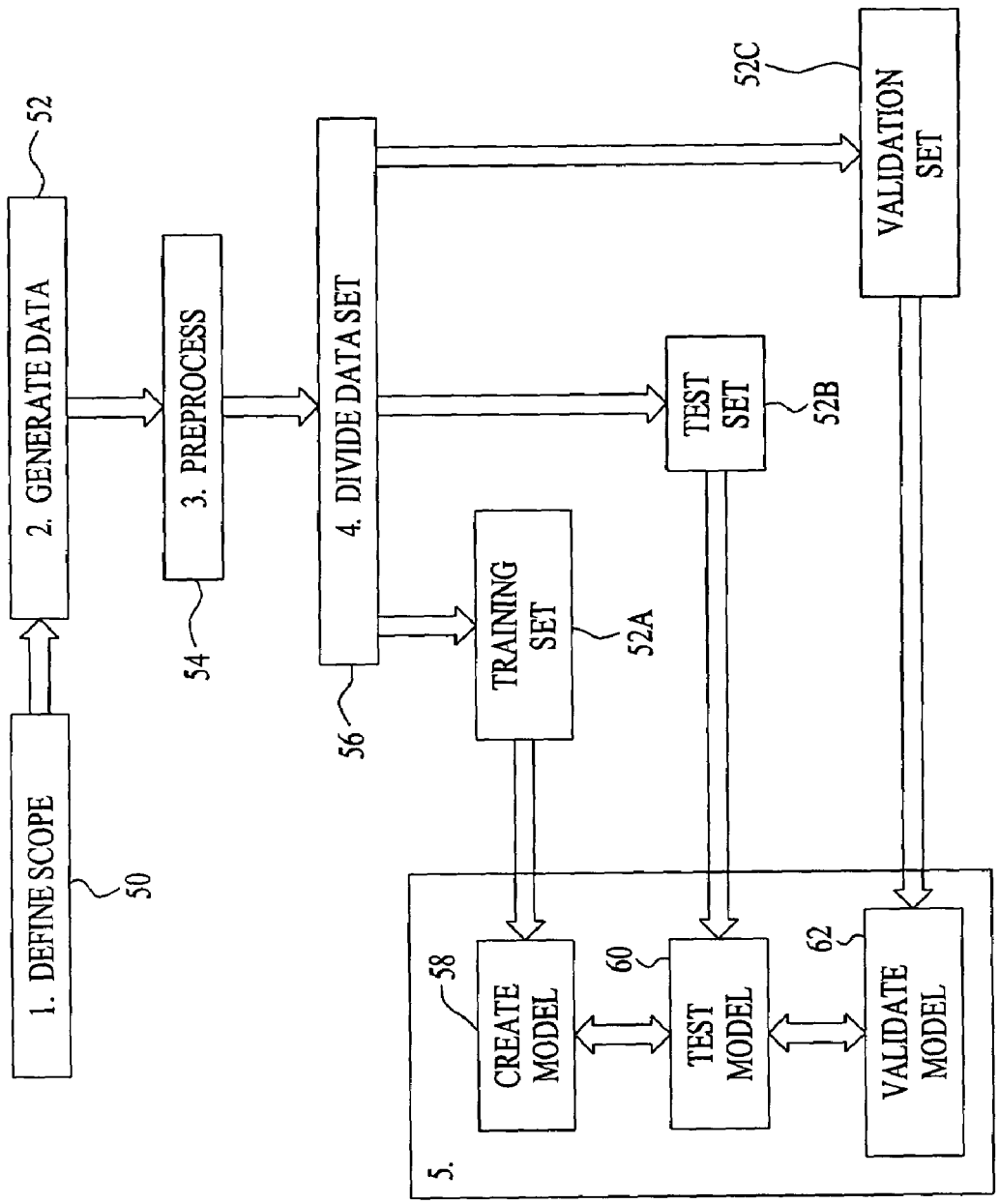
FIG. 2 illustrates the process of developing an algorithm for transforming sample data into a value representing hydrocarbon contamination.
Figure 6:
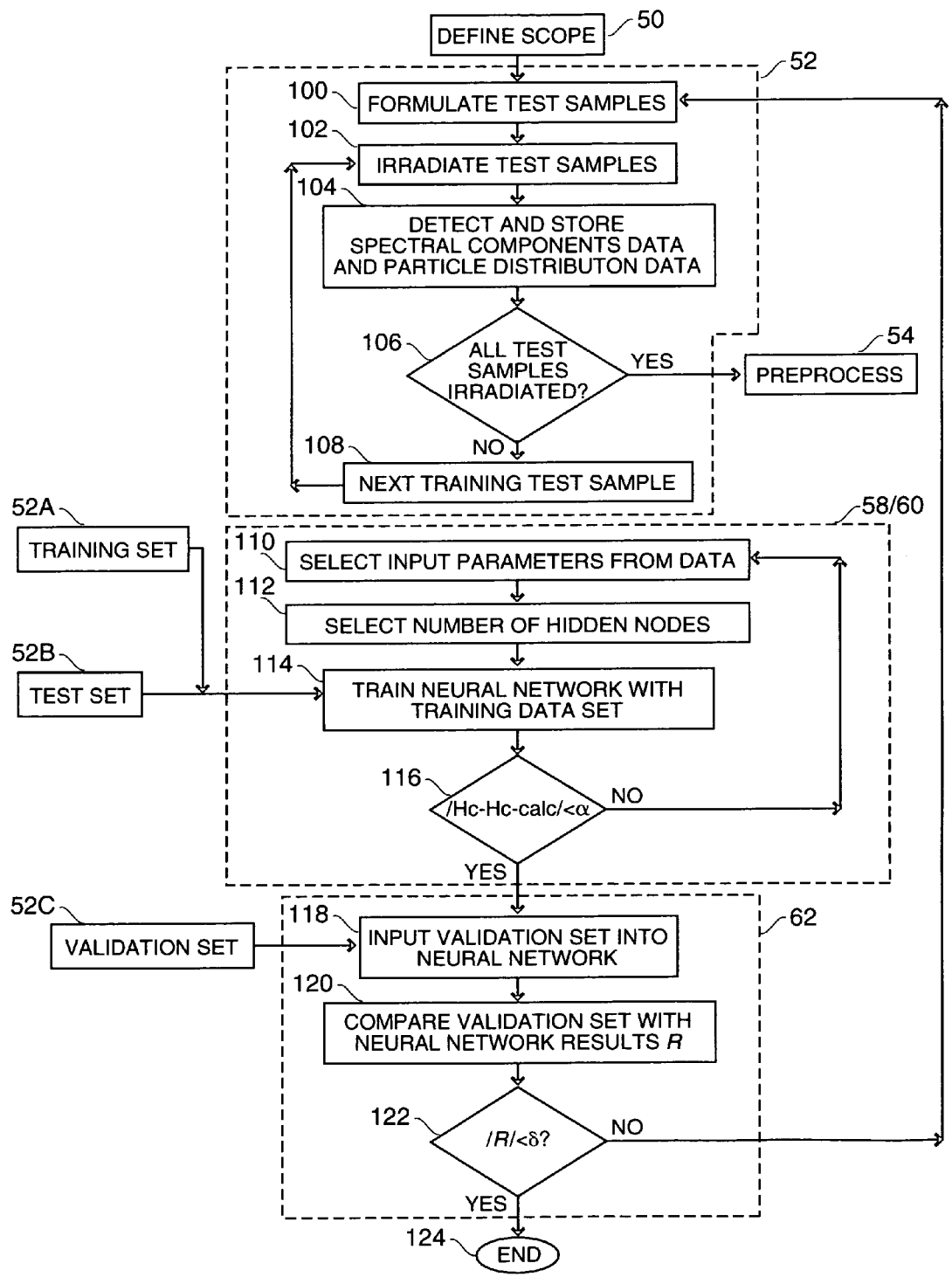
FIG. 6 is a flow chart that illustrates an embodiment of a process for developing a calibration algorithm using a neural network.

Next, at step 52, and still referring to FIGS. 2 and 6, various test samples 13 (which may include a water and/or sea water matrix) having different types and levels of hydrocarbon contamination and particle size distributions that span the defined scope of such characteristics are formulated. Also at step 52, spectral component data and particle size distribution data are generated for each test sample using system 10. The test samples 13 are placed in test cell 12 and irradiated by light signal 16. Any fluorescent or "spectral" emission signals 17 generated by irradiation of the test samples 13 are detected by spectral detector 22 as described above. Data that represents spectral emission signals 17 are provided by signal 24 to processor 42 for storage. Also, the test samples 13 are irradiated by coherent light signal 32 that is generated by coherent light source 30. Any particulates 34 that are suspended in test samples 13 cause light signals 32 to scatter and be transformed into scattered light signals 36 which are detected by multi-angle detector 38. Data representing the locations where scattered light signals 36 irradiate the multi-angle detector 38 are provided as signal 40 to processor 42 for storage. Software implemented in processor 42 determines the particle size distribution of each test sample 13.

For example, data record number one of the data set shown in FIG. 3 represents a sample mixture of sea water contaminated with 5 ppm of marine diesel fuel (DFM). Data record numbers 3 and 4 represent mixtures of sea water contaminated with jet fuel (JP5). Data record number 1 is characterized by spectra data, i.e., fluorescent emission intensity at different wavelengths, and the volume concentrations or size distributions of oil droplets 34. More specifically, data record number one represents an actual sample of seawater contaminated with 5 parts per million (ppm) of DFM. Measured fluorescent relative intensities for sample 1 at 280 nm, 300 nm, and 320 nm are 35, 56, and 17, respectively. For purposes of illustration which are presented by way of example only, FIG. 3 shows 5 data records associated with 5 different test samples of contaminated water or sea water that are used to derive the calibration algorithm. Fluorescent data generated by each aqueous sample 13 is used to construct data records such as the ones shown in FIG. 3. However, the actual development of the calibration algorithm may employ any suitable number of data records, the number of which may be much greater than five. In general, the calibration algorithm will more accurately relate spectral characteristics and particle sizes to values of hydrocarbon contamination when hundreds, and even thousands of data records are used to derive the algorithm. In addition, each data record may contain many more fluorescence intensity values than the three shown, as well as a greater number of volume concentrations (i.e., size distributions) than as shown in FIG. 3. In general, the hydrocarbons detected by embodiments described herein and used to develop the calibration algorithm include diesel fuel, jet fuel, and lubricating oils such as 9250 and 2190 lubricating oils. However, the hydrocarbons detected by embodiments described herein may also include aviation fuel, gasoline, hydraulic fluid, crude oil, and fuel oil.

At step 54, raw data such as shown in FIG. 3 is converted to a more usable form through normalization, scaling, and/or mean centering to create more robust calibration models for development of the calibration algorithm. At step 56, the data shown in FIG. 2 is divided into three independent groupings. One data record is used to train or develop the calibration algorithm, the second set is used during the training process to test the algorithm, and the third set is used to validate the calibration algorithm. The derivation of the calibration algorithm assumes that the hydrocarbon concentration content $H_c$ of aqueous sample 13 is a function of the spectral components of fluorescent emission signals 17 and particle size distribution of oil droplets 34. It is to be noted that particle size distribution may be derived using standard techniques such as optical scattering or image analysis.

Next at step 58 shown in FIG. 2, the calibration algorithm is derived. There are many mathematical techniques suitable for developing the calibration algorithm. Examples of suitable techniques include multiple linear regression, multiple nonlinear regression, principle components regression, partial least squares regression, and recursive least squares regression. The preferred method for developing the calibration algorithm includes the use of artificial neural networks. Artificial neural networks, such as back propagation, provide a convenient and powerful means of fusing multivariate, generally nonlinear, spectral and droplet size data, such as found in the data vector presented by way of example in FIG. 3, and transforming the data into an oil content value. Still other methods include using a look-up table, or a nearest-neighbor classifier.

The calibration algorithm may be developed using a three layer back-propagation neural network (BPNN) using NeuralWorks Professional II Plus by NeuralWare, Inc. and a Pentium II 450-MHz PC with 128 MB-RAM. Although the calibration algorithm was developed using a three-layer back-propagation neural network, it is to be understood that other types of neural networks may also be used. By way of example, the BPNN may include input, hidden, and output layers. The output layer of the BPNN has a single node (neuron) corresponding to oil content in parts per million (ppm). The input layer has a single node for each of the input values that comprise each data record in the data vector as shown in FIG. 3. For example, in FIG. 3, each data record includes three fluorescent emission data and three volume concentrations for three droplet size ranges. Thus, using the example of the data vector in FIG. 3, BPNN has six input nodes (neurons) corresponding to the fluorescence intensities at three different wavelengths and the volume concentrations for three droplet size ranges for each data record. Although not shown, the input layer may also include additional nodes or neurons for optical transmission and the scattering intensity at the same angle as the fluorescent detection for each data record. The BPNN transfer function used by each node is preferably a sigmoid or hyperbolic tangent, although other functions may also be used. The optimal number of nodes in the hidden layer is determined during the training process by trial and error and by iterative improvement, as for example, by trying different numbers of nodes in the hidden layers until the user is satisfied with the results. Seven hidden layers were found to provide satisfactory results for developing the calibration algorithm. The data set in FIG. 3 is split into a training data set, a test data set, and a validation data set, as exemplified in FIG. 2. The BPNN is trained using standard, well known methodology for adjusting weight parameters ultimately selected for the final version of the calibration algorithm.

Once the weights are determined so that BPNN provides satisfactory results, the BPNN is considered to be "trained," whereupon the calibration algorithm then is defined as a sequence of mathematical functions that employ the weights developed by the BPNN generally as coefficients. Satisfactory results are defined where the absolute value of the difference between the calculated value of $H_{c\text{-}calc}$ and the actual value of $H_c$ for a particular data record is less than some acceptable limit $\delta$, i.e., $|H_{c\text{-}calc} - H_c| \leq \delta$, where $H_{c\text{-}calc}$ represents the calculated hydrocarbon concentration content of aqueous sample 13 that is determined by the calibration algorithm. The calibration algorithm is characterized as a multivariate calibration algorithm because it employs multiple data inputs, as for example six inputs from each data record of FIG. 3, in order to determine the level of contamination of test sample 13. However, it is to be understood that the calibration algorithm may employ any number of data inputs as required to suit the requirements of a particular application. The algorithm may be implemented in software for execution by processor 42, or may alternatively be implemented in hardware if faster performance is desired.

Once the calibration algorithm has been successfully tested, then the third data set may be inserted into the algorithm to validate the algorithm, and thereby provide a separate, independent check of the validity of the algorithm. The difference between testing and validation data is that validation data is not used to develop the model. If a calibration model does not perform to the desired degree of accuracy with the validation set, then the model is improved using the training and test data records. After being validated, the calibration algorithm may be implemented in processor 42 for processing data.

FIG. 6 shows step 52 in greater detail where at step 100 the test samples 13 are formulated. Each of the test samples may include different concentrations of hydrocarbon contaminants and different particle size distributions, which are all known. Next, as described above, a particular test sample 13 is irradiated by light signal 16 so that spectral emission data and particle size distribution data are generated. At step 104, spectral emission data and particle size distribution data are stored by processor 42. A determination is made at step 106 as to whether spectral component and particle distribution data have been generated and stored for all of the test samples 13. If the determination at step 106 is NO, i.e., that spectral component and particle distribution data have not been generated and stored for all of the test samples 13, the process returns to step 102. If however, the determination at step 106 is YES, i.e., that spectral component and particle distribution data have been generated and stored for all of the test samples 13, the process continues to step 54.

Still referring to FIG. 6, steps 58 and 60 (collectively illustrated in FIG. 6 as 58/60), in applications where a neural network is used to develop the calibration algorithm, may include step 110 where input parameters are selected from the data generated at step 52. Such parameters may include particular fluorescence intensities and particular size volume concentrations, rather than others. For example, with regard to Data Record No. 1 in FIG. 3A, input parameters for DFM may be selected for fluorescence intensities at 280 nm and 320 nm, and particle size distribution volume concentrations at 2–5 microns and 5–10 microns rather than fluorescence intensity at 300 nm and a particle size volume concentration of 10–20 microns. Then at step 112, the number of hidden nodes in the back propagation algorithm is selected. For example, in one embodiment, seven hidden nodes have been found to provide satisfactory results. Proceeding next to step 114, the nerual network is trained using the training set provided from step 52A and the test set provided from step 52B. The neural network employs iterative techniques as described above in an attempt to provide a calibration algorithm that provides satisfactory results. A determination as to whether satisfactory results are obtained from the neural network is made at step 116 where the results of comparing the calculated output $H_{c\text{-}calc}$ of the calibration algorithm with the corresponding values $H_c$ of the test set. training set. If $|H_c - H_{c\text{-}calc}| < \alpha$, then the calibration algorithm is determined to be acceptable and the process continues to step 62, where $\alpha$ represents an error value. If however, $|H_c - H_{c\text{-}calc}| \geq \alpha$, then the calibration algorithm is not deemed to be adequately trained and the process returns to step 110.

An embodiment of step 62 shown in FIG. 2 is exemplified in more detail in FIG. 6 and as described below. The validation data set from step 52C (FIG. 2) is provided as input into the neural network at step 118. The at step 120, the validation data set is compared with the results R obtained by inputting the validation set into the neural network trained at steps 58/60. If $|R| < \delta$, the validity of the neural network is confirmed, $\delta$ represents an error value, and the process ends at step 124. If, however, $|R| \geq \delta$, then the neural network has not been validated, whereupon the process continues to step 100.

In the operation of sensor 10, data signals 24 and 40 are input into processor 42 whereupon processor 42 determines the particle size distribution of oil droplets in aqueous sample 13 from information encoded in signal 40. Then, the calibration algorithm is executed by processor 42 to calculate $H_{c\text{-}calc}$ which estimates the actual hydrocarbon concentration content $H_c$ in aqueous sample 13 from spectral data of fluorescent emission signals 17 encoded in signal 24 and the particle size distributions. Processor 42 generates an output signal 44 that represents $H_{c\text{-}calc}$ which is provided to display 46. Then display 46 presents the calculated level of hydrocarbon concentration content $H_{c\text{-}calc}$ in human readable form, such as in a textual and/or alpha/numeric format.

In practice, sensor 10 may be placed so that the aqueous sample 13 flows through the sample cell 12. For example, for bilge monitoring applications the sample stream 13 is typically the aqueous effluent of an oil-water separator. The user determines the data acquisition rate, i.e. the number of measurements per unit time. The detection of light signals 17 and 36 and processing of signals 24 and 40 may be performed by processor 42 on a time scale of a few seconds or less, whereupon the presentation of display 46 is updated after each measurement.

Figure 4:
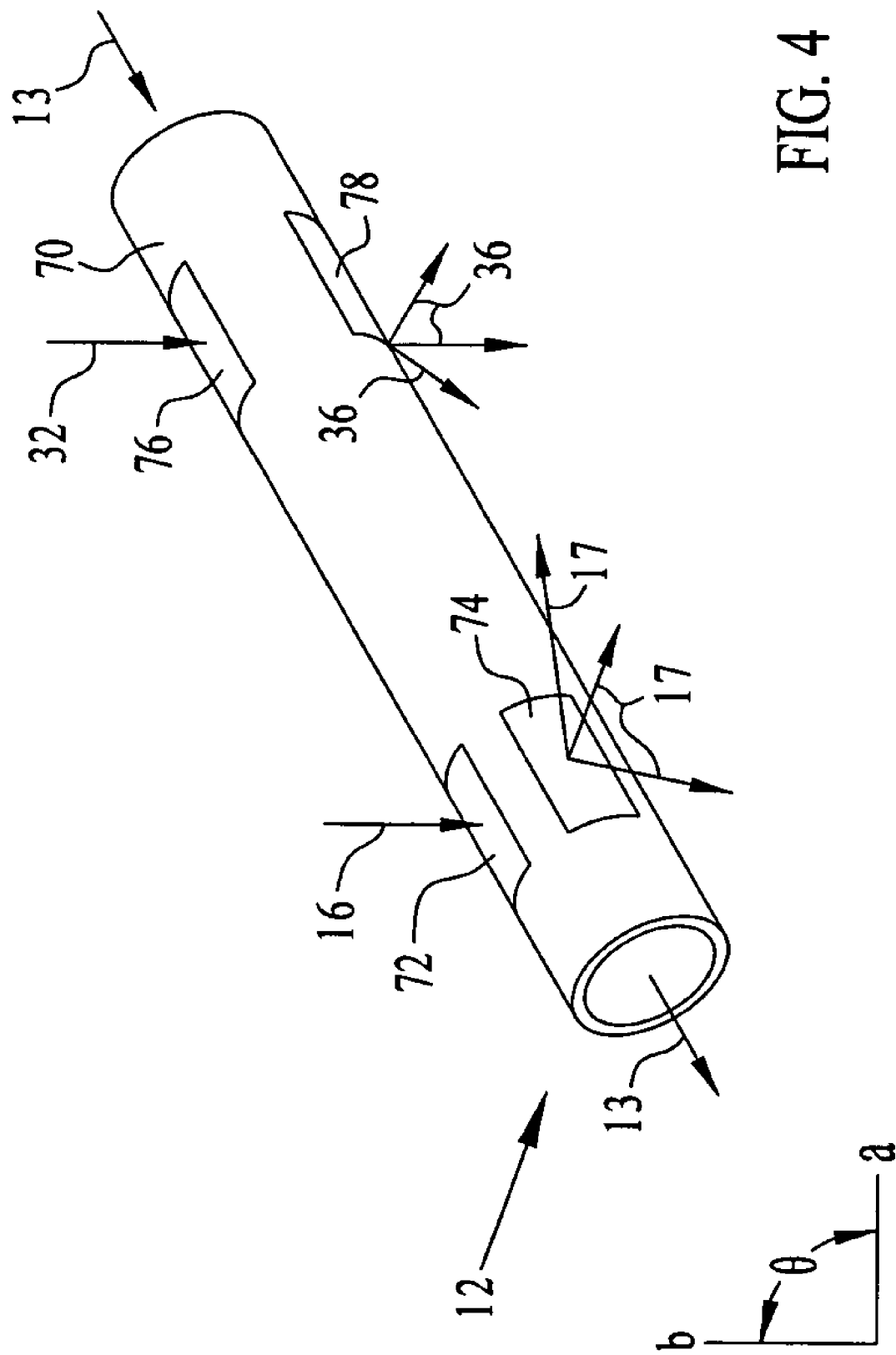
FIG. 4 shows a second embodiment of the sample cell.

In another embodiment, shown in FIG. 4, sample cell 12 may be implemented as a tube 70 in which are mounted windows 72, 74, 76, and 78, which may be made of quartz or glass. Fluorescent excitation light signal 16 enters window 72 and if any hydrocarbons that are present in test sample 13 are irradiated by light signal 16, the fluorescent light signals 17 will be emitted out of tube 70 through window 74 for detection by spectral detector 22. Windows 72 and 74 are preferably offset radially by an angle $\theta$, such as 90° with respect to reference axes a and b so that the propagation direction of fluorescent excitation light signal 16 does not transect both windows 72 and 74 in order to prevent light signal 16 from entering the field of view of spectral detector 22. Coherent light signal 32 enters window 76 and if signal 32 irradiates any emulsified oil droplets 34, light signal 32 is transformed into scattered light signals 37 which are emitted from tube 70 through window 78. Windows 76 and 78 may preferably be mounted diametrically opposed to each other in tube 70 as shown in FIG. 4, however, such a configuration is not necessary. Tube 70 may be made of stainless steel because stainless steel has excellent chemical resistance to the types of contaminants likely to be found in test sample 13.

Figure 5:
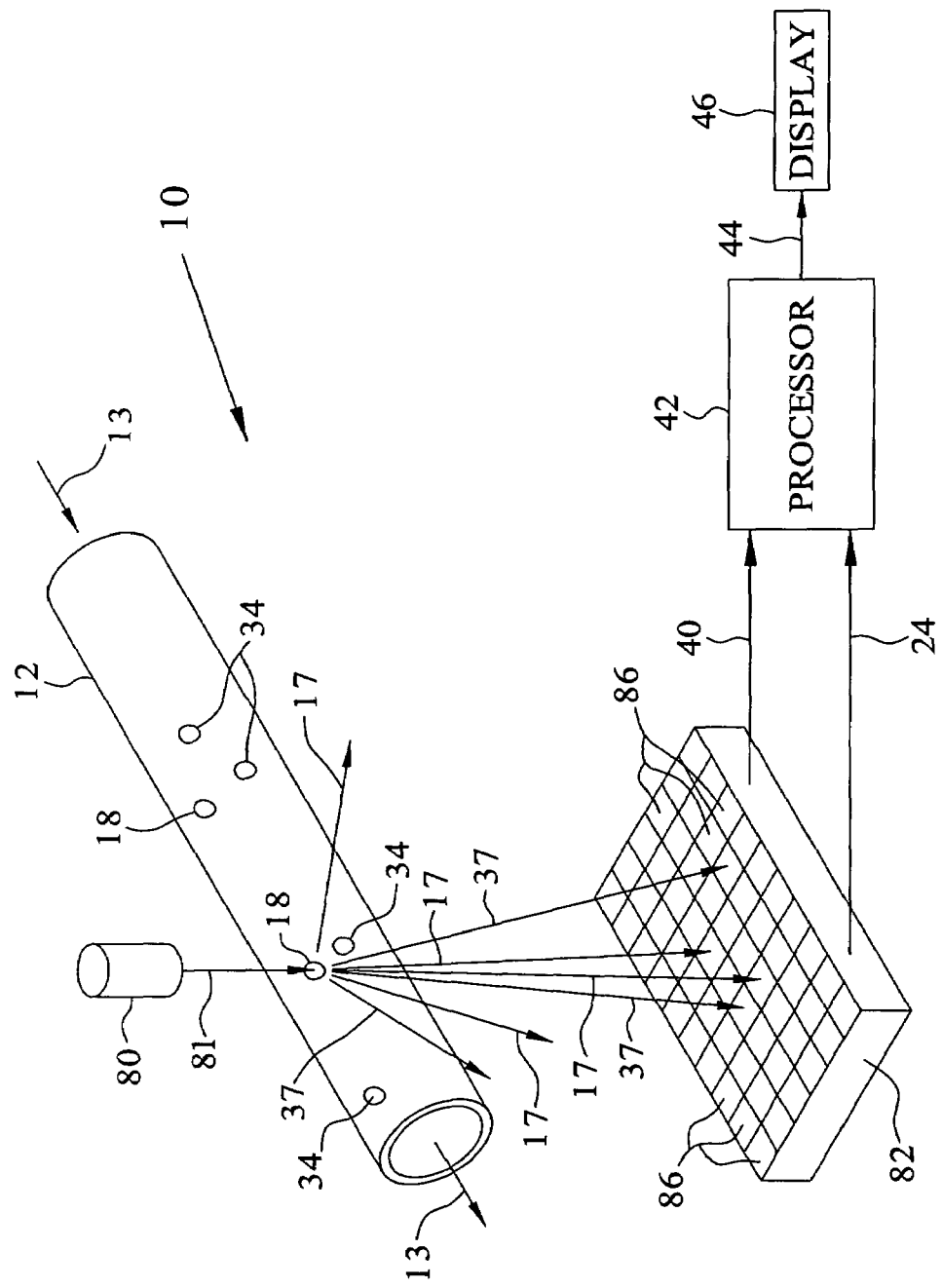
FIG. 5 shows an embodiment of the present invention that includes a single excitation optical energy source.

FIG. 5 illustrates another embodiment of system 10 which includes sample cell 12 through which flows aqueous sample 13. An ultraviolet coherent light source 80 generates an ultraviolet coherent light signal 81 that is directed into sample cell 12. UV light signal 81 stimulates fluorescent emission signals 17 from any hydrocarbons 18 that may be present in the aqueous sample 13 that are irradiated by light signal 81. Spectral photo detector 82, such as a CCD array having optical sensing elements 86, detects fluorescent emission signals 17 and the intensities and locations where scatter light signals 37 irradiate photo detector 82. Scatter light signals 37 are produced as a result of UV light signal 81 irradiating particular oil droplets 36 in aqueous sample 13. Photo detector 82 generates a signal 24 that represents selected spectral characteristics of fluorescent emission signals 17. In the embodiment of sensor 10 shown in FIG. 5, the field of view of photo detector 82 may detect UV light signal 81. The effect of signal 81 irradiating photo detector 82 may be nulled because the optical sensing elements 86 that are irradiated by UV signal 81 may be taken off-line or by appropriate use of algorithms executed in processor 42. Photodetector 82 generates electrical signals, collectively referenced as signal 40 from locations on the photodetector 82 where the scattered light signals 37 irradiate light detecting elements 86 of photo detector 82. Signal 40 represents the intensities and scatter angles of light signals 37 that are detected by photo detector 82. Software executed in processor 42 employs the information encoded in signal 40 to determine the size distribution of oil droplets 34 in aqueous test sample 13 using well known techniques. Because photo detector 82 detects both fluorescent emission signals 17 and scattered light signals 37, only one optical energy source is required.

Processor 42 implements an algorithm that uses the particle size distribution of oil droplets 34 previously determined by processor 42 using intensity and scatter angle information encoded in signal 40, and the spectral component information from flourescent emission signals 17 represented in signal 24 to determine a value $H_{c\text{-}calc}$ representing the hydrocarbon concentration content $H_c$ of hydrocarbons 34 present in the aqueous test sample 13.

Implementation of this algorithm by processor 42 results in the generation of an output signal 44 representing the hydrocarbon concentration content $H_{c-calc}$ of oil in test sample 34 that is provided to display 46. Display 46 presents $H_{c-calc}$ in human readable form, as for example, "Oil content=25 ppm."

In another embodiment of sensor 10, raw data encoded in signal 40, which represents intensity and location data corresponding to the locations on detector 38 that are irradiated by scattered light signals 37, may be directly input into the BPNN to develop the calibration algorithm in lieu of using the particle size distribution data as inputs into the BPNN. Therefore, processor 42 may execute the algorithm to determine the hydrocarbon content $H_{c-calc}$ of aqueous test sample 13 directly from information encoded in signals 24 and 40, without having to determine the particle size distribution of particulates 34. In this embodiment, the calibration algorithm estimates the hydrocarbon content $H_{c-calc}$ based on the fluorescent emission signals 17 and the scattering light signals 37, and does not employ the particle size distribution to estimate $H_{c-calc}$.

Obviously, many modifications and variations of the present invention are possible in light of the above teachings. For example, particle size distributions may also be determined based on optical imaging and other techniques. It is therefore to be understood that within the scope of the appended claims, the invention may be practiced otherwise than as specifically described.

We claim:

1. A method for quantifying the hydrocarbon concentration content of aqueous media, comprising the steps of:

generating a coherent ultraviolet light signal that stimulates fluorescent emissions when said coherent ultraviolet light signal irradiates any hydrocarbons present in an aqueous sample in a sample cell, where said coherent ultraviolet light signal is transformed into scattered light signals when said coherent ultraviolet light irradiates hydrocarbons in said aqueous sample;

generating a first electrical signal that represents spectral components of said fluorescent emissions in response to detecting said fluorescent emissions that are emitted from said sample cell, and for generating a second electrical signal in response to detecting scattered light signals emitted from said sample tube, where said second electrical signal represents the intensities and scatter angles of said scattered light signals; and determining a particle size distribution of said hydrocarbons from said second electrical signal and the hydrocarbon concentration content of said aqueous sample from said first electrical signal and said particle size distribution.

2. The method of claim 1 wherein the step of determining said particle size distribution of said hydrocarbons and said hydrocarbon concentration content of said aqueous sample implements a calibration algorithm.

3. The method of claim 2 wherein said calibration algorithm is developed by the steps of:

irradiating aqueous test samples that contains hydrocarbons and particulates with light signals so that fluorescent emission signals and scattered light signals are emitted from each of said aqueous test samples, wherein said fluorescent emission signals are characterized by intensities at selected wavelengths, and said scattered light signals are characterized by intensities at scatter angles;

detecting said fluorescent emission signals and said scattered light signals;

generating first data signals that represent said intensities of said fluorescent emission signals, and second data signals that represent said intensities and scatter angles of said second data signal;

storing representations of said first and second data signals to create a data set;

dividing said data set into a training data set, a test data set, and a validation data set;

selecting input parameters from said data set;

defining a neural network having a selected number of hidden nodes;

training said neural network using said training data set and said test data set; and validating said neural network using said validation data set.

4. The method of claim 2 wherein said calibration algorithm is developed by the steps of:

irradiating aqueous test samples that contains hydrocarbons and particulates with a light signal so that fluorescent emission signals and scattered light signals are emitted from each of said aqueous test samples, wherein said fluorescent emission signals are characterized by intensities at selected wavelengths, and said scattered light signals are characterized by intensities at scatter angles;

detecting said fluorescent emission signals and said scattered light signals;

generating first data signals that represent said intensities of said fluorescent emission signals, and second data signals that represent said intensities and scatter angles of said second data signal;

storing representations of said first and second data signals to create a data set;

dividing said data set into a training data set, a test data set, and a validation data set;

selecting input parameters from said data set;

defining a neural network having a selected number of hidden nodes;

training said neural network using said training data set and said test data set; and validating said neural network using said validation data set.

* * * * *